(12) United States Patent
Sakamoto et al.

(10) Patent No.: US 6,664,418 B1
(45) Date of Patent: Dec. 16, 2003

(54) METHOD FOR INHIBITING POLYMERIZATION OF A VINYL COMPOUND

(75) Inventors: Kazuhiko Sakamoto, Hyogo-Ken (JP);
Kazuo Ohkouchi, Hyogo-Ken (JP);
Masahiro Uemura, Hyogo-Ken (JP);
Sei Nakahara, Hyogo-Ken (JP);
Masatoshi Ueoka, Hyogo-Ken (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/361,183

(22) Filed: Jul. 27, 1999

(30) Foreign Application Priority Data

Jul. 27, 1998 (JP) ............................................. 10-210505
Jul. 27, 1998 (JP) ............................................. 10-210506

(51) Int. Cl.[7] .......................... C07C 57/18; C07C 69/52; C07C 51/42
(52) U.S. Cl. ........................ 562/598; 562/600; 560/205
(58) Field of Search .......................... 560/205; 562/598, 562/600

(56) References Cited

U.S. PATENT DOCUMENTS

| | | |
|---|---|---|
| 4,127,603 A | 11/1978 | Bljumberg et al. |
| 5,322,960 A | 6/1994 | Sakamoto et al. |
| 5,504,243 A * | 4/1996 | Sakamoto et al. .......... 560/205 |
| 5,728,872 A | 3/1998 | Riemenschneider |
| 5,856,562 A | 1/1999 | Mine et al. |
| 5,877,344 A | 3/1999 | Gande et al. |
| 5,932,735 A * | 8/1999 | Cunkle et al. .............. 546/242 |

FOREIGN PATENT DOCUMENTS

| | | |
|---|---|---|
| CN | 1052847 A | 7/1991 |
| EP | 0 620 206 | 10/1994 |
| EP | 0 620 206 A1 | 10/1994 |
| EP | 0 685 447 | 12/1995 |
| EP | 0 685 447 A2 | 12/1995 |
| GB | 1127127 | 9/1968 |
| GB | 1 346 775 | 2/1974 |
| JP | 56-38301 | 4/1981 |
| JP | 60-36501 | 2/1985 |

OTHER PUBLICATIONS

Zhao Ciyi, et al., "The Synthesis of β–hydroxy Ethyl Methacrylate and Distillation Polymerization Inhibitor Thereof," *Journal of WUHAN Chemical Industry College*, vol. 17, No. 4, pp. 20–23 w/English Abstract.

Z. Li, et al., Chemistry of Synthetic High Polymers, CA 129:316591, 1 page, "Inhibiting Effect on the Radical Polymerization of Vinyl Monomers," 1997 (Abstract Only).

* cited by examiner

*Primary Examiner*—Alan L. Rotman
*Assistant Examiner*—Taylor V. Oh
(74) *Attorney, Agent, or Firm*—Oblon, Spivak, McClelland, Maier & Neustadt, P.C.

(57) ABSTRACT

A method for inhibiting polymerization during transportation, storage and/or production of (meth)acrylic acid or an ester thereof includes adding an N-oxyl compound and water to a vinyl compound; or dissolving an N-oxyl compound in water and adding the solution to a vinyl compound in a process of recovering, purifying, and/or synthesizing of the vinyl compound. The method can effectively inhibit polymerization of the vinyl compound.

10 Claims, No Drawings

METHOD FOR INHIBITING POLYMERIZATION OF A VINYL COMPOUND

BACKGROUND OF THE INVENTION

1. Field of the Invention

The present invention relates to a method for inhibiting polymerization of a vinyl compound. More particularly, the present invention relates to a method for effectively inhibiting the polymerization of (meth)acrylic acid or esters of (meth)acrylic acid during these storage, transportation and production.

2. Description of the Prior Art

Vinyl compounds such as (meth)acrylic acid (i.e., acrylic acid or methacrylic acid), esters of (meth)acrylic acid, and acrylonitrile are prone to be naturally polymerized by light or heat due to the vinyl bond they have. Therefore, there have been proposed to use various polymerization inhibitors in order to inhibit polymerization of (meth)acrylic acid or esters of (meth)acrylic acid during their storage, transportation or production process.

As an example, there has been proposed use of methoquinone. Japanese Examined Patent Publication No. 414121 discloses a method for inhibiting polymerization of vinyl compounds using an N-oxyl compound such as bis-(2,2,6,6-tetramethyl-4-piperidino oxyl) sebacate.

However, the inventors of the present application have studied the stability of a vinyl compound during storage or transportation after addition of the above-mentioned N-oxyl compound, and found that the concentration of the N-oxyl compound gradually decreases in contact with the vinyl compound, and it is difficult to prevent polymerization of vinyl compounds for a prolonged time.

In the production process of vinyl compounds, particularly in the processes of recovery, purification and synthesis of vinyl compounds, polymerization of vinyl compounds proceeds. Therefore, there have been proposed to use various polymerization inhibitors in order to inhibit the polymerization of (meth)acrylic acid or esters of (meth)acrylic acid during these processes.

For example, Japanese Examined Patent Publication No. 45-1054 discloses a method for inhibiting polymerization of acrylic acid using an N-oxyl compound such as tertiary-butyl nitroxide and 4-hydroxy-2,2,6,6-tetramethyl-4-piperidino oxyl alone, gives better polymerization inhibiting effect than that of the conventionally known hydroquinone, pheno-thiazine, and cupric chloride etc.

Japanese Examined Patent Publication No. 54-3853 discloses a method for inhibiting the polymerization using 4-hydroxy-2,2,6,6-tetramethylpiperidino oxyl or 2,2,6,6-tetramethylpiperidino oxyl in the production process of methacrylic acid from methacrolein using a gas containing oxygen in an organic solvent.

Japanese Examined Patent Publication No. 58-46496 discloses a method for inhibiting polymerization of (meth) acrylic acid or esters of (meth)acrylic acid, using 3-oxo-2,2,5,5-tetramethyl pyrolidino oxyl or 4-acetoxy 2,2,6,6-tetramethylpiperidino oxyl.

Chinese Patent CN 1052847A discloses a method for inhibiting polymerization of acrylic acid and esters of acrylic acid, using 4-hydroxy-2,2,6,6-tetramethylpiperldino oxyl alone or used in combination with hydroquinone, which is shown to be higher than the effect of combined use of copper dibutyldithiocarboxylate and hydroquinone.

Japanese Unexamined Patent Publication No. 6-345681 discloses a method for inhibiting polymerization of acrylic acid and esters of acrylic acid, using N-oxyl compounds such as 2,2,6,6-tetramethylpiperldino oxyl, and 4,4',4"-tris (2,2,6,6-tetramethylpiperldino oxyl) phosphate in combination with phenol compounds such as hydroquinone, and phenothiazine compound.

Japanese Unexamined Patent Publication No. 9-316026 discloses a method for inhibiting polymerization of acrylic acid and esters of acrylic acid during its production, particularly during distillation process, using an N-oxyl compound in combination with phosphorus compound.

In the use of N-oxyl compounds according to the conventional polymerization inhibiting technology in the production process, for example, to prevent polymerization during distillation of crude acrylic acid, an N-oxyl compound is dissolved in acrylic acid and the solution is transferred to a distilling column by a pump.

The inventors found that the transfer of the solution, in which the N-oxyl compound is dissolved in acrylic acid, to the distilling tower in the recovery, purification and synthesis process of vinyl compound as mentioned above does not sufficiently inhibit the polymerization of vinyl compound.

SUMMARY OF THE INVENTION

It is an object of the present invention to provide a method for inhibiting polymerization of a vinyl compound which has overcome the problems residing in the prior art.

It is another object of the present invention to provide a method for stabilizing and inhibiting polymerization of vinyl compounds such as (meth)acrylic acid and ester of (meth)acrylic acid which can reliably assure stabilization and inhibition of polymerization of such vinyl compounds during storage, transportation and production of them, in the presence of an N-oxyl compound and a specific amount of water.

According to an aspect of the present invention, a method for inhibiting polymerization of a vinyl compound uses an N-oxyl compound and a specific amount of water. The presence of the N-oxyl compound can inhibit polymerization of the vinyl compound more effectively.

According to another aspect of the present invention, an N-oxyl compound is dissolved in water to produce a solution, and the solution is added to a vinyl compound in a process of recovering, purifying, or synthesizing the vinyl compound. In this way, polymerization of the vinyl compound can be effectively inhibited.

The vinyl compound has a vinyl bond which is liable to cause polymerization. Also, the N-oxyl compound includes any water soluble N-oxyl compounds.

DETAILED DESCRIPTION OF THE PREFERRED EMBODIMENTS

The present invention is directed to inhibition of polymerization of (meth)acrylic acid and esters of (meth)acrylic acid.

Acrylic esters include methyl acrylate, ethyl acrylate, butyl acrylate, 2-ethylhexyl acrylate, 2-hydroxyethyl acrylate, 2-hydroxypropyl acrylate and the like. Also, methacrylic esters include methyl methacrylate, propyl methacrylate, 2-hydroxyethyl methacrylate, 2-hydroxypropyl methacrylate and the like.

According to the present invention, any water soluble N-oxyl compounds is useable. It is preferable to use 2,2,6,6-tetramethylpiperidino oxyls represented by the following general formula (1);

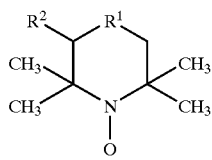

wherein R[1] represents CHOH, CHCH$_2$OH, CHCH$_2$CH$_2$OH, CHOCH$_2$OH, CHOCH$_2$CH, OH, CHCOOH or C=O, R[2] represents H or CH$_2$OH.

The above-mentioned 2,2,6,6-tetramethylpiperidino oxyls include 4-hydroxy-2,2,6,6-tetramethylpiperidino oxyl, 4-oxo-2,2,6,6-tetramethylpiperidino oxyl, 4-carboxy-2,2,6, 6-tetramethylpiperidino oxyl, and the like. Among these, preferably used are 4-hydroxy-2,2,6,6-tetramethylpiperidino oxyl, 4-oxo-2,2,6,6-tetramethylpiperidino oxyl, and the like, and particularly preferably used is 4-hydroxy-2,2,6,6-tetramethylpiperidino oxyl. These N-oxyl compounds may be used singly or at least two of these compounds may be used in combination. In this case, the mixing ratio may be appropriately decided.

More specifically, an N-oxyl compound may be preferably added in an amount of 0.0005 parts by weight or more, more preferably 0.001 parts by weight or more, to 100 parts by weight of a vinyl compound in order to ensure sufficient stabilization effects. On the other hand, addition of an N-oxyl compound too much causes staining in a produced acrylic acid. Accordingly, the amount may be preferably to set an upper limit up to 0.1 parts by weight, more preferably up to 0.03 parts by weight.

The adding amount of water may be adjusted in accordance with the solubility of water in the vinyl compound. It may be, however, preferable to dissolve 0.01 parts by weight or more of water to 100 parts by weight of the vinyl compound, more preferably 0.02 parts by weight or more, more preferably 0.05 parts by weight or more. To assure the inhibiting effect, on the other hand, it may be preferable to set the upper limit amount of water at 20 parts by weight, preferably 5 parts by weight, more preferably 2 parts by weight. If the adding amount of water is less than 0.01 parts by weight, it is difficult to regulate the concentration of the N-oxyl compound to a specified value, resulting in decomposition of the N-oxyl compound and consequently insufficient inhibition effect. While too much water will lower the stabilization effect thereof, as water promotes the polymerization of the vinyl compound, therefore the amount of water added shall be up to 20 parts by weight.

The addition of N-oxyl compound and water to a vinyl compound is not limited to a fixed sequence, but may be changed desirably. However, it may be preferable -that an N-oxyl compound is firstly dissolved in water and then the resulting N-oxyl compound aqueous solution is added to a vinyl compound. Also, it may be possible to add an N-oxyl compound into a mixture of a vinyl compound and water. In this way, there coexist three components, i.e., N-oxyl compound, vinyl compound and water. It could be presumed that this coexistence of the three components exerts the polymerization inhibiting effect.

The present invention may be applicable to vinyl compounds which contain impurities as by-product in the production process, or impurities contained in the starting raw materials of a vinyl compound. For acrylic acid containing various impurities, e.g., organic acids such as acetic acid, aldehydes such as acrolein, for example, the inhibiting effect can be attainable.

Further, it may be possible to use conventional polymerization inhibitors such as phenothiazine, methoquinone, copper dialkyldithiocarbamate, manganese acetate, and p-phenylenediamine, in addition to the inventive polymerization inhibitor.

Owing to the coexistence of an N-oxyl compound and a specific amount of water in a vinyl compound, the decrease in the concentration of the N-oxyl compound can be suppressed for a prolonged time. The coexistence of an N-oxyl compound and a specific amount of water in a vinyl compound delays the time for initiating polymerization more than the conventional inhibitors, thus inhibiting polymerization of a vinyl compound in the storage or transportation more effectively.

Further, a method for inhibiting -the polymerization, according to the present inventive method, during production of a vinyl compound will be explained in detail.

A vinyl compound in a process of recovery, purification and synthesis is kept from polymerizing by dissolving an N-oxyl compound in water, and adding the solution into the vinyl compound.

Conventionally, acrylic acid is produced from a reaction gas obtained by two stage catalytic oxidation reaction of propylene by the processes of: (1) collecting an acrylic acid in the form of an aqueous solution by making a reaction mixture gas containing acrylic acid in contact with water; (2) distilling the acrylic acid aqueous solution in the presence of an azo-tropic solvent and recovering crude acrylic acid; and (3) purifying the crude acrylic acid. The purifying process (3) includes distillation of separating substances having low boiling points such as acetic acid, distillation of separating substances having low boiling points such as unreacted acrolein, and distillation of separating substances having high boiling points.

The present invention is applicable for inhibition of polymerization of acrylic acid in any of the above-mentioned processes i.e., (1) collecting process, (2) recovering process, and (3) purifying process.

The addition of an aqueous solution of an N-oxyl compound is not limited to a particular manner, but may be carried out in a desired manner. For example, the aqueous solution of N-oxyl compound may be directly introduced into a vinyl compound in each process. In the case of purifying processor also, it may be introduced into in a supply line or a refluxing line.

An aqueous solution of an N-oxyl compound may be added only in the collecting process (1), or in each of the processes of collecting process (1), recovering process (2) and purifying process (3) (including various distillations). It may be preferable to add the aqueous solution in each process or each distillation stage.

In the case of adding -the aqueous solution in each process, it may be preferable to set the lower limit of adding amount of N-oxyl compound at 0.0005 parts by weight, more preferably 0.001 parts by weight, more preferably 0.002 parts by weight to 100 parts by weight of a vinyl compound in each process. The upper limit may be preferable to set at 0.1 parts by weight, more preferably 0.03 parts by weight, more preferably 0.02 parts by weight to 100 parts by weight of vinyl compound in each process.

If the adding amount of N-oxyl compound is less than 0.0005 parts by weight, the necessary polymerization inhibiting effect cannot be attained. In particular, if the operation temperature is more than 100° C., the inhibiting effect noticeably lowers. On the other hand, if an N-oxyl compound is added more than 0.1 parts by weight, the product of acrylic acid is liable to be stained.

The amount of water in which an N-oxyl compound is dissolved may be changed in accordance with the kind and the amount of an N-oxyl compound used as well as the kind of process. However, it may be preferable to set the lower limit at 0.0005 parts by weight, more preferably 0.001 parts by weight, more preferably 0.002 parts by weight to 100 parts by weight of a vinyl compound in each process. If the amount of water is more than 10 parts by weight, on the other hand, the purity of the product of acrylic acid undesirably lowers. Accordingly, the upper limit for water may be set at 10 parts by weight, preferably 1 part by weight, more preferably 0.2 part by weight.

The concentration of an N-oxyl compound in an N-oxyl compound aqueous solution may be regulated in accordance with the kind of N-oxyl compound or the allowable amount of water. However, it may be preferable to set the upper limit at around 80 percent of the saturation solubility of the N-oxyl compound in water at a normal temperature to prevent precipitation of the N-oxyl compound in a tank storing the N-oxyl compound aqueous solution. On the other hand, the lower limit of the concentration of a N-oxyl compound depends on the amount of the N-oxyl compound to be added or the characteristic performance of an adding apparatus. However, it may be preferable to set the lower limit at around 0.1 weight percent.

The effect of inhibiting polymerization of a vinyl compound in the production process according to the present invention is not obtained simply because water coexists with the N-oxyl compound in each process or in each distillation stage. According to the present invention, regardless of the presence of water in the production process, the use of water as a solvent for N-oxyl compound, which means the N-oxyl compound is dissolved in water first and the aqueous solution is then added to the above-described process, is significant condition to exert the effect of inhibiting polymerization of a vinyl compound in the production process.

For example, in the collecting process (1), water is introduced to collect an acrylic acid. In the recovering process (2), the acrylic acid aqueous solution is introduced and distilled. Accordingly, water exists in each process location or tower. However, in the collecting process (1), the case in which an N-oxyl compound is added in the form of an aqueous solution inhibits polymerization of acrylic acid more effectively than the case in which the N-oxyl compound is added in the form of an acrylic acid solution (see Example 5 and Comparative Example 2). Accordingly, it could be seen that the addition of an N-oxyl compound in the form of an aqueous solution, which is in accordance with a method of the present invention, enhances the polymerization inhibiting effect of N-oxyl compound.

As mentioned above, in the collecting process (1) and the recovering process (2), there exists water. However, water is separated in each process. Accordingly, even if water exists in relatively large amount in these processes, there is no problem. On the contrary, in the distillation stage of -the purifying process (3), the amount of water should be kept in the specified range to prevent the purity of the product from lowering.

For example, in the collecting process (1) and the recovering process (2), the amount of water may be 1–1000 times by weight that of an N-oxyl compound, and in the purifying process (3), the amount of water may be 1–200 times by weight that of an N-oxyl compound in a distillation stage for separating substances having a low boiling point, and it is 1–50 times by weight in a distillation stage for separating substances having a high boiling point.

According to the present invention, molecular oxygen may be used concurrently, thereby enhancing the inhibition of polymerization of a vinyl compounds. As means of supplying molecular oxygen, it may be possible to adopt bubbling, or alternatively dissolve molecular oxygen in a solvent, and add the solution in a vinyl compound. For example, in the purifying process (3), molecular oxygen may be supplied from the bottom of a stripper tower or reboller in the form of gas. It may be preferable to supply molecular oxygen in an amount of 0.1 percent by volume or more with respect to the amount of evaporated vinyl compound. This is because of the fact that if it is less than 0.1 percent by volume, remarkable effect cannot be attainable. The upper limit of molecular oxygen to be supplied may be determined based the operation performance of distilling equipment. However, a large amount of supply requires reconstruction of the equipment. Accordingly, it may be preferable to supply molecular oxygen in not more than 1.0 percent by volume.

In addition to acrylic acid, the present invention may be applicable to other vinyl compounds.

The term "production", "recovering", "purifying", and "synthesizing" means the reaction process of a vinyl compound, and the above-mentioned processes (1)–(3). Further, such terms include a modification of the abovementioned process and any additional distilling process for separating a substance having a specified boiling point and the like.

In the case of acrylic acid, these terms respectively correspond to an oxidation process of propylene, recovering, purifying and synthesizing processes of acrylic acid. In the case of methacrylic acid, these terms respectively correspond to processes of separating, collecting, refining methacrylic acid from a reaction gas containing methacrylic acid obtained by catalytic gas phase oxidation of isobutylene. In the case of (meth)acrylic ester, these terms respectively correspond to processes of esterifying and purifying in addition to the above-mentioned processes of (meth)acrylic acid.

The present invention will be further described with reference to the following Examples. All the ppm is based on weight.

EXAMPLE 1

A solution in which water in an amount of 2-0 parts by weight to 100 parts by weight of acrylic acid to be treated, and 4-hydroxy-2,2,6,6-tetramethylpiperldino oxyl (hereinafter abbreviated as 4H-TEMPO) in an amount of 0.03 parts by weight to 100 parts by weight of the acrylic acid were dissolved in acrylic acid was stored at the room temperature in a sample bottle and the concentration of 4H TEMPO in the acrylic acid was measured 30 minutes, 2 hours and 10 hours after the dissolution. The results were as follows. No decrease in the concentration of 4H-TEMPO was observed even after 10 hours.

Initial amount: 300 ppm
After 30 minutes: 300 ppm
After 2 hours: 300 ppm
After 10 hours: 300 ppm

EXAMPLE 2

The concentration of 4H-TEM-PO in acrylic acid was measured in a process similar to that of Example 1, except that the amount of water added was 0.03 parts by weight to 100 parts by weight of the acrylic acid. The results are as follows: About 60% of the initial concentration of 4H-TEMPO still remained after 2 hours and about 34% of the initial concentration of 4H-TEMPO still remained after 10 hours.

Initial amount: 300 ppm
After 30 minutes: 204 ppm
After 2 hours: 174 ppm
After 10 hours: 103 ppm

EXAMPLE 3

The concentration of 4H-TEMPO in acrylic acid was measured in a process similar to that of Example 1, except that the amount of water added was 0.1 parts by weight to 100 parts by weight of the acrylic acid. The results are as follows: About 80% of the initial concentration of 4H-TEMPO still remained after 2 hours and About 60% of the initial concentration of 4H-TEMPO still remained after 10 hours.

Initial amount: 300 ppm
After 30 minutes: 275 ppm
After 2 hours: 243 ppm
After 10 hours: 180 ppm

COMPARATIVE EXAMPLE 1

The concentration of 4H-TEMPO in acrylic acid was measured in a process similar to that of Example 1, except that the amount of water added was 0.005 parts by weight to 100 parts of the acrylic acid. The results are as follows: The concentration of 4H-TEMPO reduced to one third of the initial concentration after 2 hours and about 3% of the initial concentration of 4H-TEMPO remained after 10 hours.

Initial amount: 300 ppm
After 30 minutes: 152 ppm
After 2 hours: 98 ppm
After 10 hours: 10 ppm From the comparison of the Examples 1–3 with the Comparative Example 1, it is clear that when a specific amount of water is added together with 4H-TEMPO, the reduction in the concentration of 4H-TEMPO with time can be controlled and the acrylic acid can be stably maintained.

EXAMPLE 4

5 ml of a solution comprising acrylic acid, water in such an amount that is given in Table 1 and 4H-TEMPO in an amount of 0.0001 parts by weight to 100 parts by weight of acrylic acid was added to a test tube and immersed in an oil bath which was kept at 80° C. and the time required until the viscosity starts to increase was measured as the -time for initiating polymerization. The results are given in Table 1.

TABLE 1

| Sample No. | Amount of water added (parts by weight) | Time for initiating polymerization (hour) |
| --- | --- | --- |
| 1 | 2 | 50 |
| 2 | 5 | 36 |
| 3 | 10 | 30 |
| 4 | 15 | 27 |
| 5 | 25 | 19 |
| 6 | 43 | 15 |
| 7 | 67 | 8 |
| 8 | 100 | 7 |
| 9 | 150 | 4 |

Note: The amount of water added is based on weight to 100 parts by weight of the acrylic acid As seen from Table 1, in Samples in which the amount of water added is up to 20 parts by weight to 100 parts by weight of acrylic acid, i.e., Sample Nos. 1–4, the time for initiating polymerization was 25 hours or more, however, when more than 20 parts by weight of water were added (No. 5–No. 9), the time for initiating polymerization was less than 20 hours. In Samples in which water of up to 5 parts by weight were added, ±.e., Sample Nos. 1 and 2, the time for initiating polymerization was at least 35 hours or more, showing that the range is more preferable for inhibiting the polymerization of acrylic acid more effectively at an elevated temperature.

By employing the polymerization inhibiting method of the present invention, the induction time can be extended longer than before, and polymerization can be more effectively inhibited.

EXAMPLE 5

The effect of inhibiting polymerization in the collecting process (1) was confirmed.

Propylene was subjected to gas phase oxidation using a gas containing molecular oxygen in the presence of an oxidizing catalyst to give a reaction mixture gas comprising 0.68 kg/hr of acrylic acid, 0.02 kg/hr of acetic acid and 0.45 kg/hr of water. The reaction mixture gas was introduced to a gas collecting tower in which a cascade mini ring (inner diameter of 14 mm) was packed by a height of 6000 mm, a gas blow-off tube was provided at the top of the tower, a reaction mixture gas supply pipe at the lower part of the tower, and a tower bottom liquid extract pipe at the bottom of the tower, and the collection operation of the reaction mixture gas was carried out using water as an absorbing liquid.

During the collection process, 4-hydroxy-2,2,6,6-tetramethylpiperidino oxyl aqueous solution was used as a polymerization inhibitor and an aqueous solution thereof was introduced at 0.02 kg/hr from the top of the tower. The amount of the polymerization inhibitor used was 0.003 parts by weight to 100 parts by weight of the acrylic acid and the amount of water used was 2.9 parts by weight to 100 parts by weight of the acrylic acid.

The operation was carried out at the tower top temperature of 63° C., tower bottom temperature of 67° C. and acrylic acid aqueous solution of 0–6 kg/hr was obtained through the bottom of the tower in the stationary state. The polymerization inhibition effect was confirmed by the viscosity of the liquid taken out through the bottom of the tower and the examination of the overhauled tower.

The operation was carried out continuously under the above-mentioned conditions for about 20 days and always stable condition was obtained and no generation of a polymer was found at all when the collecting tower was examined after the operation was stopped.

COMPARATIVE EXAMPLE 2

The collection operation was carried out in the same way as that used in Example 4 except that 4-hydroxy-2,2,6,6-tetramethylpiperidino oxyl was used as a polymerization inhibitor which was dissolved in acrylic acid and added.

7 days after the start of the operation the viscosity of the liquid taken out through the bottom of the tower was observed to increase. The operation was stopped and the tower was overhauled and the generation of the polymer was observed in the tower.

EXAMPLE 6

The polymerization inhibiting effect in the recovering process (2) was confirmed. Acrylic acid aqueous solution was distilled using a packed tower having an outlet pipe, a refluxing liquid supply pipe and a polymerization inhibitor solution supply pipe at the top of the tower, a raw material supply pipe at the middle of the tower, and a kettle, a tower bottom liquid extract pipe and an oxygen supply pipe at the bottom of the tower. The acrylic acid aqueous solution was an acrylic acid aqueous solution containing 30% by weight of water which was obtained by contacting water with a reaction mixture gas obtained by catalytic gas phase oxidation of propylene. The acrylic acid aqueous solution was supplied to the above-mentioned packed tower at 100 ml/hr. Distillation was carried out using toluene as a refluxing liquid, under such conditions that tower top pressure of 190 mmHg, tower top temperature of 50° C., and tower bottom temperature of 100° C.

A polymerization inhibitor of a given amount was added to and dissolved in a solvent as shown in Table 2, then the obtained polymerization inhibiting solution was added from the top of the tower into the packed tower and oxygen gas of 0–3% by volume based on the amount of the evaporated acrylic acid vapor was supplied to the bottom of the tower. The amount of the polymerization inhibitor added was based on the amount of the acrylic acid supplied to the packed tower. The composition of the liquid taken out from the bottom of the tower in the steady state comprised 97% by weight of acrylic acid, 0.02% by weight of water and 2.98% by weight of others. As the refluxing liquid, the distilled oil phase was recycled and used. After operating for 8 hours, inside of the tower was dried by aspirating with a vacuum pump having minimum pressure of $5 \times 10^{-4}$ Torr from the lower part of the tower for 15 hours at a room temperature, and the weight of the polymer generated in the tower was measured to evaluate the polymerization inhibiting effect. The results are given in Table 2.

TABLE 2

| Sample No. | Polymerization inhibitor (Note 1) Kind | Amount (ppm) | Solvent used for dissolving the polymerization inhibitor (Note 2) | Amount of produced polymer (g) |
|---|---|---|---|---|
| 1 | 4H-TEMPO | 100 | Water | 0.9 |
| 2 | Same as above | 50 | Water | 1.7 |
| 3 | Same as above | 100 | Refluxing liquid (toluene) | 3.8 |
| 4 | Same as above | 100 | Acrylic Acid | 5.8 |
| 5 | 4-Oxo-TEMPO | 100 | Water | 0.8 |
| 6 | Same as above | 100 | Refluxing liquid (toluene) | 4.0 |
| 7 | Same as above | 100 | Acrylic acid | 1 |

(Note 1) The amount of polymerization inhibiting agent was based on weight to 100 parts by weight of acrylic acid.
(Note 2) Each solvent was supplied in an amount of 0.82 parts by weight to 100 parts by weight of acrylic acid in the raw material.

The abbreviations used in Table 2 represent the following compounds. The same abbreviations are made in Tables 3, 4, and 5.

4H-TEMPO: 4-hydroxy-2,2,6,6-tetramethylpiperldino oxyl
4-Oxo-TEMPO: 4-oxo-2,2,6,6-tetramethylpiperldino oxyl.

As it is clear from Table 2, 4H-TEMPO dissolved in water and added (Sample Nos-1, 2 and 5) inhibits the polymerization of acrylic acid effectively as a smaller amount of a polymer is generated compared to the case in which the agent is dissolved in toluene or acrylic acid and added.

EXAMPLE 7

Distillation of an acrylic acid aqueous solution was carried out in the process similar to that used in Example 6 except that methyl isobutyl ketone was used as the refluxing liquid. The results are given in Table 3.

TABLE 3

| Sample No. | Polymerization inhibitor (Note 1) Kind | Amount (ppm) | Solvent used for dissolving the polymerization inhibitor (Note 2) | Amount of produced polymer (g) |
|---|---|---|---|---|
| 1 | 4H-TEMPO | 100 | Water | 1.2 |
| 2 | Same as above | 50 | Water | 2.6 |
| 3 | Same as above | 100 | Refluxing liquid (methyl isobutyl ketone) | 5.4 |
| 4 | Same as above | 100 | Acrylic Acid | 8.9 |
| 5 | 4-Oxo-TEMPO | 100 | Water | 1.3 |
| 6 | Same as above | 100 | Refluxing liquid (methyl isobutyl ketone) | 6.7 |
| 7 | Same as above | 100 | Acrylic acid | 9.5 |

(Note 1) The amount of polymerization inhibiting agent was based on weight to 100 parts by weight of acrylic acid.
(Note 2) Each solvent was supplied in an amount of 0.82 parts by weight to 100 parts by weight of acrylic acid in the raw material.

As it is clear from Table 3, 4H-TEMPO dissolved in water and added (sample Nos. 1, 2 and 5) inhibits the polymerization of acrylic acid effectively as a smaller amount of a polymer is generated compared to the case in which the agent is dissolved in methyl isobutyl ketone or acrylic acid and added.

EXAMPLE 8

Distillation of an acrylic acid aqueous solution was carried out in the process similar to that used in Example 6 except that a mixed solvent of methyl isobutyl ketone and toluene (mixed at 65:35 by weight) was used as the refluxing liquid. The results are given in Table 4

TABLE 4

| Sample No. | Polymerization inhibitor (Note 1) Kind | Amount (ppm) | Solvent used for dissolving the polymerization inhibitor (Note 2) | Amount of produced polymer (g) |
|---|---|---|---|---|
| 1 | 4H-TEMPO | 100 | Water | 0.3 |
| 2 | Same as above | 50 | Water | 0.9 |
| 3 | Same as above | 100 | Refluxing liquid (methyl isobutyl ketone + toluene) | 2.4 |
| 4 | Same as above | 100 | ketone + toluene) | 3.7 |
| 5 | 4-Oxo-TEMPO | 100 | Acrylic Acid | 0.3 |
| 6 | Same as above | 100 | Water | 2.9 |
| 7 | Same as above | 100 | Refluxing liquid (methyl isobutyl ketone + toluene) Acrylic acid | 4.1 |

(Note 1) The amount of polymerization inhibiting agent was based on weight to 100 parts by weight of acrylic acid.
(Note 2) Each solvent was supplied in an amount of 0–82 parts by weight -to 100 parts by weight of acrylic acid in the raw material.

As it is clear from Table 4, 4H-TEMPO dissolved in water and added (No. 1, No. 2 and No. 5) inhibits the polymerization of acrylic acid effectively as a smaller amount of a polymer is generated compared to the case in which the agent is dissolved in the mixed solvent of methyl isobutyl ketone and toluene or acrylic acid and added.

EXAMPLE 9

Distillation of an acrylic acid aqueous solution was carried out in the process similar to that used in Example 6 except that a mixed solvent of methyl methacrylate and toluene (mixed at 35:65 by weight) was used as the refluxing liquid. The result is given in Table 5.

TABLE 5

| Sample No. | Polymerization inhibitor (Note 1) | | Solvent used for dissolving the polymerization inhibitor (Note 2) | Amount of produced polymer (g) |
|---|---|---|---|---|
| | Kind | Amount (ppm) | | |
| 1 | 4H-TEMPO | 100 | Water | 0.2 |
| 2 | Same as above | 50 | Water | 0.7 |
| 3 | Same as above | 100 | Refluxing liquid (methyl methacrylate + toluene) | 2.1 |
| 4 | Same as above | 100 | toluene) | 3.5 |
| 5 | 4-Oxo-TEMPO | 100 | Acrylic Acid | 0.3 |
| 6 | Same as above | 100 | Water | 2.8 |
| 7 | Same as above | 100 | Refluxing liquid (methyl methacrylate + toluene) Acrylic acid | 4.5 |

(Note 1) The amount of polymerization inhibiting agent was based on weight to 100 parts by weight of acrylic acid.
(Note 2) Each solvent was supplied in an amount of 0.82 parts by weight to 100 parts by weight of acrylic acid in the raw material.

As it is clear from Table 5, 4H-TEMPO dissolved in water and added (No. 1, No. 2 and No. 5) inhibits the polymerization of acrylic acid effectively as a smaller amount of a polymer is generated compared to the case in which the agent is dissolved in the mixed solvent of methyl methacrylate and toluene or acrylic acid and added.

The present invention can be carried out in various other forms without departing from the spirit and main features thereof. Therefore, the above-mentioned Examples are considered as illustrative only in every aspect and cannot be understood to limit the present invention. The scope of the present invention is shown by the claims and the text of the specification does not restrict it in any way. All the modifications and equivalents may be regarded as falling within the scope of the invention in the appended claims and -their equivalents.

EXAMPLE 10

5 ml of a solution comprising acrylic acid water in such an amount that is given in Table 6 and 4H-TEMPO in an amount of 0.001 parts by weight to 100 parts by weight of acrylic acid was added to a test tube and immersed in an oil bath which was kept at 80° C. and the time required until the viscosity starts to increase was measured as the time for initiating polymerization. The results are given in Table 6.

TABLE 6

| Sample No. | Amount of water added (Parts by weight) | Time for initiating polymerization (hour) |
|---|---|---|
| 1 | 1.5 | 614 |
| 2 | 4 | 435 |
| 3 | 15 | 307 |
| 4 | 30 | 148 |
| 5 | 100 | 65 |

Note: The amount of water added is based on weight to 100 parts by weight of the acrylic acid.

As seen in Table 6, in Samples in which the amount of water added is up to 20 parts by weight to 100 parts by weight of acrylic acid, i.e., Sample Nos 1–2, the time for initiating polymerization was 300 hours or more, however, when more than 20 parts by weight of water were added (No.4 and No. 5), the time for initiating polymerization was less than 150 hours. In Samples in which water of up to 5 parts by weight were added, i.e., Sample Nos. 1 and 2, the time for initiating polymerization was at least 400 hours or more, showing that the range is more preferable for inhibiting the polymerization of acrylic acid more effectively at an elevated temperature.

By employing the polymerization inhibiting method of the present invention, the induction time can be extended longer than before, and polmerization can be more effectively inhibited.

The priority documents of the present application, Japanese Patent Application Nos. 10-210505 and 10-210506 filed Jul. 27, 1998, are hereby incorporated by reference.

What is claimed is:

1. A method for inhibiting polymerization of a vinyl compound selected from the group consisting of (meth) acrylic acid and esters of (meth)acrylic acid, during its storage and/or its transportation comprising permitting a water soluble N-oxyl compound and 0.01–2 parts by weight of water to coexist in 100 parts by weight of the vinyl compound, wherein the N-oxyl compound is at least one selected from the group consisting of N-oxyl compounds represented by the following general formula:

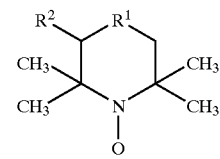

wherein $R^1$ represents $CHOH$, $CHCH_2OH$, $CHCH_2CH_2OH$, $CHCOOH$ or $C=O$, $R^2$ represents H or $CH_2OH$.

2. A method according to claim 1, wherein the water soluble N-oxyl compound and the water are added to the vinyl compound.

3. A method according to claim 1, wherein the water is added to a mixture of the water soluble N-oxyl compound and the vinyl compound.

4. A method according to claim 1, wherein the water soluble N-oxyl compound is added to a mixture of the water and the vinyl compound.

5. A method according to claim 1, wherein the vinyl compound is a (meth)acrylic acid.

6. A method according to claim 1, wherein the water soluble N-oxyl compound is added in 0.0005–0.1 parts by weight to 100 parts by weight of the vinyl compound.

7. A method for inhibiting polymerization of a vinyl compound selected from the group consisting of (meth) acrylic acid and esters of (meth)acrylic acid, comprising the steps of:

(i) dissolving an N-oxyl compound in water, the amount of water being 1 to 1000 times by weight that of the N-oxyl compound; the amount of water being 0.0005 to 10 parts by weight per 100 parts by weight of the vinyl compound; and the amount of the N-oxyl compound being 0.0005 to 0.1 parts by weight per 100 parts by weight of the vinyl compound; and (ii) adding the solution to the vinyl compound in a process of recovering, purifying, and/or synthesizing of the vinyl compound.

8. A method according to claim 7, wherein the vinyl compound is a (meth)acrylic acid.

9. A method according to claim 7, wherein the N-oxyl compound is one or more kinds selected from the groups consisting of N-oxyl compounds represented by the following general formula;
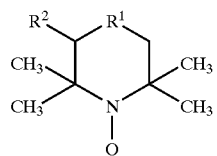
wherein $R^1$ represents $CHOH$, $CHCH_2OH$, $CHCH_2CH_2OH$, $CHOCH_2OH$, $CHOCH_2CH_2OH$, $CHCOOH$ or $C=O$, $R^2$ represents H or $CH_2OH$.
10. A method according to claim 7, wherein the solution is added in a collecting stage, a distilling stage and/or a purifying stage of the process of recovering, purifying, and/or synthesizing of the vinyl compound.
* * * * *